United States Patent [19]

Göler et al.

[11] Patent Number: 5,159,080

[45] Date of Patent: Oct. 27, 1992

[54] INDOLE COMPOUNDS, A PROCESS FOR THEIR PREPARATION, AND PHARMACEUTICAL COMPOSITIONS CONTAINING THEM

[75] Inventors: Klaus Göler; Wolf Grimminger, both of Bergisch Gladbach; Karl P. Odenthal, Grevenbroich, all of Fed. Rep. of Germany; Pierre Potier, Paris, France

[73] Assignee: Madaus AG, Cologne, Fed. Rep. of Germany

[21] Appl. No.: 629,188

[22] Filed: Dec. 18, 1990

Related U.S. Application Data

[63] Continuation-in-part of Ser. No. 512,060, Apr. 19, 1990, abandoned, which is a continuation of Ser. No. 320,407, Mar. 8, 1989, abandoned.

[30] Foreign Application Priority Data

Mar. 8, 1988 [DE] Fed. Rep. of Germany ....... 3807533

[51] Int. Cl.$^5$ .......................................... C07D 221/18
[52] U.S. Cl. ...................................... 546/41; 546/49; 546/70
[58] Field of Search ............................ 546/49, 70, 41; 514/279, 280, 285

[56] References Cited

PUBLICATIONS

Langlois, et al. Tetrahedron, 31, 1975 pp. 423 to 428.
Hussan, et al., Chemical Abstracts, vol. 90, 1979 Abstract 87706q.
Sauviat, Br. J. Pharmac. (1980) 7141-7149.

*Primary Examiner*—Robert T. Bond
*Attorney, Agent, or Firm*—Felfe & Lynch

[57] ABSTRACT

Compounds of the formula

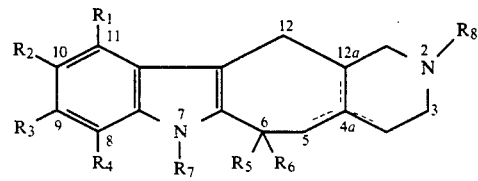

wherein $R_1$ to $R_8$, which may be identical to or different from each other, have diverse meanings, and the dotted line between the carbon atoms in the 4- and 4a- position or the 4a- and 5-position or the 42- and 12a position may be a single or double bond, or pharmaceutically acceptable salts thereof, as well as a process for the preparation of these compounds, and pharmaceutical compositions containing these compounds. The compounds and their salts are useful for the treatment of heart-circulation disorders.

1 Claim, No Drawings

INDOLE COMPOUNDS, A PROCESS FOR THEIR PREPARATION, AND PHARMACEUTICAL COMPOSITIONS CONTAINING THEM

CROSS REFERENCE TO RELATED APPLICATION

This is a continuation in part of copending application Ser. No. 512,060, filed Apr. 19, 1990; now abandoned which in turn is a continuation of application Ser. No. 320,407, filed Mar. 8, 1989, now abandoned.

FIELD OF THE INVENTION

The present invention is concerned with indole compounds, a process for the preparation thereof and pharmaceutical compositions containing these compounds.

BACKGROUND OF THE INVENTION

Blood pressure-lowering agents available include, inter alia, diuretics, vasodilators, symphatholytics, calcium antagonists, as well as conversion enzyme inhibitors. These agents act through different mechanisms and, depending upon the severity and the spectrum of the underlying disease, in some cases incompatibilities may arise and the agents cause undesirable side effects. As a result, not only may it prove necessary for a physician to discontinue a course of treatment, but it is also known for a patient to discontinue his treatment as a result of his becoming aware of certain side effects.

Accordingly, there is a requirement for an effective treatment for hypertension having a lower incidence rate of side effects such as pathological blood pressure increase, increased heart rate and ischaemic heart disease.

The indole alkaloids ervatamine (J. S. Glasby, Encyclopedia of the Alkaloids, Vol. 1. (1975) and methuenine (P. Bakana, R. Dommisse, E. Esmans, R. Fokkens, J. Totte, N. M. N. Nibbering and A. J. Vlietinck, Planta Medica, 51, 331/1984), both of which substances have a chemical structure which is similar to that of acylindoles, are known in the art. However, these substances are not known as blood pressure lowering agents or as causative agents of bradycardia.

DESCRIPTION OF THE INVENTION

We have discovered new synthetic indole compounds of the formula I which have a preponderantly α-receptor-medicated blood pressure lowering effect, and which at the same time also cause bradycardia.

Accordingly, the present invention provides indole compounds of the formula

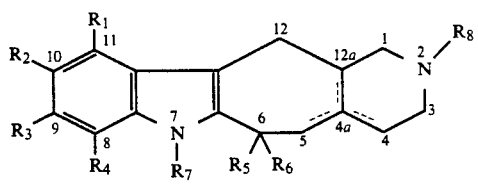

wherein $R_1$ to $R_4$, which may be the same or different, are hydrogen or halogen atoms, $C_1$-$C_4$-alkyl, halomethyl with 1 to 3 halogen atoms, $C_1$-$C_4$-alkoxy, hydroxyl, amino, $C_1$-$C_4$-alkylamino, $C_1$-$C_4$dialkylamino, $C_1$-$C_3$-alkyl sulphonamido, arylsulphonamido, $C_1$-$C_3$-acylamido, $C_1$-$C_3$-acyl, $C_1$-$C_3$-acyloxy, cyano, carboxyl, $C_1$-$C_4$-alkoxy-carbonyl, or methylenedioxy or ethylenedioxy formed by two vicinal substituents; $R_5$ and $R_6$ together are an oxo group, or one of $R_5$ or $R_6$ is a hydrogen atom and the other is $C_1$-$C_4$-alkoxy group; $R_7$ and $R_8$, which can be the same or different, are hydrogen, $C_1$-$C_4$-alkyl, benzyl or $C_1$-$C_3$-acyl groups and the broken lines between the carbon atoms in position 4 and 4a and 5 or 4a and 12a can signify a single or double bond; or a pharmaceutically acceptable salt thereof.

Preferably the above-mentioned alkyl groups (including substituted alkyl groups, such as alkoxy, alkylamino etc.), are methyl groups. Preferably the acyl group is an acetyl group. Aryl preferably signifies a phenyl group which may have substituents including one or more $C_1$-$C_4$-alkyl, $C_1$-$C_4$-alkoxy, nitro, amino or hydroxyl groups or halogen atoms.

The expression "halogen atom" includes fluorine, chlorine, bromine and iodine atoms, especially fluorine, chlorine and bromine atoms.

When the broken line between the carbon atoms is positions 4 and 4a and 5 or 4a and 12a does not signify a double bond, i.e., when only a single bond is present between these positions the hydrogen atoms in the 4a and 12a positions are preferably in the cis position to one another.

A preferred group of compounds according to the invention are those of formula (I) in which $R_1$ to $R_4$, which can be the same or different, are a hydrogen or halogen atom, a $C_1$-$C_4$-alkyl, $C_1$-$C_4$-alkoxy, hydroxyl or methylenedioxy group; or a pharmaceutically acceptable salt thereof.

A further preferred group of compounds according to the invention are those of formula (I) in which $R_1$ to $R_4$, which can be the same or different, are a hydrogen or halogen atom, or a $C_1$-$C_4$-alkyl group. $R_7$ preferably is a hydrogen atom and $R_8$ a hydrogen atom, or a $C_1$-$C_4$-alkyl group.

More preferably, $R_7$ is a hydrogen atom, $R_5$ and $R_6$ together an oxo group and $R_8$ a methyl group.

The invention also includes pharmaceutically acceptable salts of the compounds of the above formula (I). Such salts can be hydrochloric acid, sulphuric acid, phosphoric acid, or organic acids, such as maleic acid, fumaric acid, lactic acid, tartaric acid, malic acid, citric acid and the like. The preferred acid-addition salts are hydrochlorides and hemitartrates and tartrates.

When the compounds according to the invention contain acid groups, the corresponding salts with bases can also be prepared. Such bases include alkali metal and alkaline earth metal hydroxides, ammonia or organic amines, such as mono-, di- and trialkylamines, the corresponding hydroxyalkylamines and the like.

Compounds according to the invention may be prepared from the corresponding 2-acetylindole compounds. This preparation includes the following steps (in the following general formulae (I) to (V), the symbols $R_1$ to $R_8$ have the same meanings as given above.

Step A

A compound of the general formula (II)

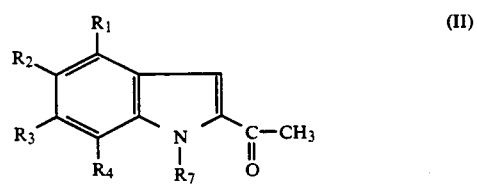

is reacted with N,N-dimethylmethyleneammonium halide, which is freshly prepared accordingly to a process known from the literature. There is thereby obtained a compound of the general formula (III):

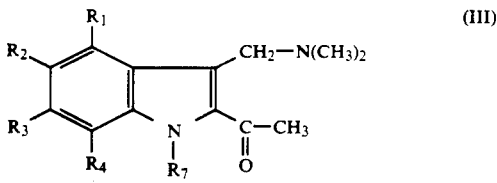

The reaction is carried out in an anhydrous solvent, such as acetonitrile, dioxan, tetrahydrofuran or the like, at room temperature or elevated temperature, for example 20° to 80° C., under an inert gas cover.

Step B

The compound of the formula (III) thus obtained is reacted with a compound of the general formula (IV):

to give a compound of the general formula (V):

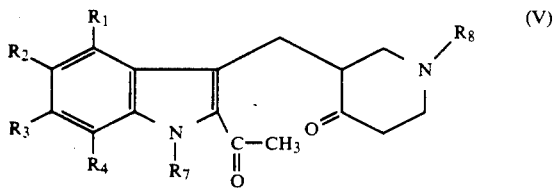

The reaction takes place in an appropriate solvent, such as acetonitrile or an ether, for example dioxan, tetrahydrofuran, ethylene glycol dimethyl ether, or a halogenated hydrocarbon, such as dichloromethane or chloroform or the like, at an elevated temperature, preferably at the reflux temperature of the solvent.

Step C

The compound thus obtained of general formula (V) is then reacted in the presence of a base to give a compound of general formula (I). Suitable bases include for example, potassium tert.-butylate, sodium tert.-butylate, sodium tert.-amylate and the like. As a solvent, there is preferably used an ether, for example tetra-hydrofuran, dioxan, ethylene glycol dimethyl ether and the like. The reaction preferably takes place at room temperature.

In the compound of formula (I) with $R_5$ and $R_6$ together being an oxo group and the broken line a double bond between the carbon atoms in the position 4 and 4a or 4a and 5 or 4a and 12a, the position of the double bond can be controlled by choice of the appropriate solvent.

If a compound of general formula (I) is desired in which the broken line is not a double bond, then an unsaturated product is hydrogenated in the presence of a conventional hydrogenation catalyst. The double bond is hydrogenated, regardless of which of the three possible positions it is present in. Appropriate hydrogenation catalysts are Pd/charcoal, Rh/charcoal, Pt/charcoal or $PtO_2$. The hydrogenation can take place at reduced or elevated temperature under atmospheric pressure or at an elevated pressure in an appropriate solvent, for example, an alcohol, such as methanol or ethanol, or an ether, such as tetrahydrofuran.

If a compound of general formula (I) is desired in which one of the symbols $R_5$ or $R_6$ signifies a hydroxyl or alkoxy group, then the above compound of general formula (I), in which $R_5$ and $R_6$ stand for an oxo group, is reduced to the corresponding hydroxyl compound and, if desired, this is then alkylated. These reactions take place in the usual way, for example, by comparatively long hydrogenation with noble metal catalysts such as mentioned above, or by reduction with the help of complex metal hydrides, such as lithium aluminum hydride or sodium borohydride, followed by alkylation with, for example, methanol, in the presence of a strong base.

The compounds according to the invention may be used for the treatment of heart-circulatory diseases in humans and animals and are especially effective in lowering blood pressure, bradycardia and in the therapy of ischaemic heart diseases.

Therefore, the invention also provides pharmaceutical agents which contain at least one of the compounds according to the invention, optionally together with pharmaceutically acceptable carriers and/or adjuvants.

The pharmaceutical agents may be formulated for administration in any suitable way. The pharmaceutical agents, incorporating compounds according to the invention, can be formulated for injection and made available in a unit dosage form in ampoules or in multiple dosage containers, if necessary with an appropriate preserving agent. The pharmaceutical agents can also be present as a suspension, solution or emulsion in oily or aqueous carriers and contain formulation adjuvants, such as suspension, stabilizing and/or dispersion agents.

The compositions according to the invention may also be administered orally, for example as tablets, capsules, dragees and the like. For the formulations in solid form, appropriate adjuvants are possibly added thereto such as starch, lubricants, for example magnesium stearate, gum arabic, talc and the like.

The compounds according to the invention can also be formulated as suppositories which contain, for example, conventional suppository bases, such as cocoa butter or other glycerides.

The compositions can contain 0.1% and more, for example 0.1 to 99% of active material, depending upon the mode of administration. If the compositions include single dosages, then each unit preferably contains 0.5 to 100 mg of active material.

The dosage for the treatment of patients depends upon the individual circumstances and is preferably in the range of 0.5 to 250 mg per day, depending upon the individual circumstances and the degree of severity of the disease. The application can take place orally or parenterally.

The agents according to the invention can also be administered in combination with other therapeutic agents, for example other heart-circulation agents or diuretics.

The invention also concerns compounds of the general formula (V):

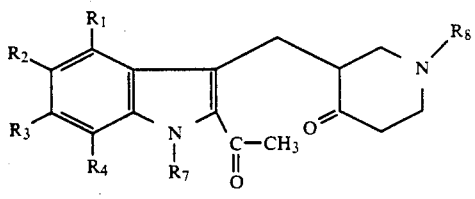

wherein preferably $R_1$, $R_2$, $R_3$, $R_4$, and $R_7$ are hydrogen and $R_8$ is a methyl group: formula VI (SI-WG 331).

These compounds have a pharmacological action similar to that of the aforementioned compounds of general formula I.

The following Examples are given for the purpose of illustrating the present invention:

EXAMPLE 1

Preparation of the compound 1,3,4,4a,5,7,12, 12a-octa-hydro-2-methyl-2H-pyrido [3',4':4,5] cyclohept [1,2-b]-indol-6-one

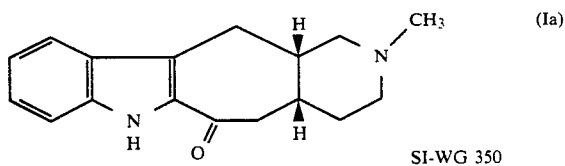

Step A: 2-Acetyl-3-(N,N-dimethylaminomethyl)-indole (SI-WG 343)

187 g (2 mols) N,N-dimethylmethyleneammonium chloride are suspended under an inert gas (nitrogen or argon) in 28 liters anhydrous acetonitrile. The stirred suspension is mixed with 159 g (1 mol) pulverized and dried 2-acetylindole, heated to the boil and, while stirring continuously, uniformly cooled over the course of 7 hours to 25° C. It is stirred overnight at 20°-25° C. The acetonitrile is substantially distilled off under vacuum and the remaining residue taken up in 20 liters of water and adjusted to pH 9-10 with concentrated ammonium hydroxide solution. This solution is stirred up three times with, in each case, 5 liters of dichloromethane. The organic phases are combined and washed with 5 liters of water. The organic phase is dried by the addition of anhydrous sodium sulphate, filtered and mixed with 5 liters tert-butyl methyl ether. The dichloromethane is substantially distilled off, the crystallization of the product thereby already commencing. This is completed by leaving to stand overnight at +4° C. The product is filtered off with suction, washed with n-hexane and dried under a vacuum. Yield: 141.7 g (65.6% of theory).

In the same way and with the use of appropriately substituted 2-acetylindoles of general formula (II), there were obtained the following compounds of general formula (IIIa):

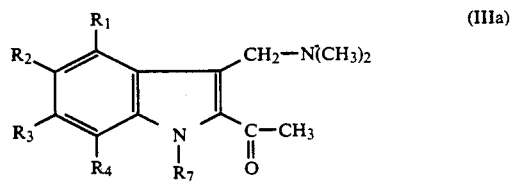

The compounds of general formula (IIIa) are summarized in Table 1.

Step B: 2-Acetyl-3-(N.methyl-4-'-piperidon-3'-ylmethyl)-indole (SI-WG 331)

140.4 g (0.65 mol) of the compound obtained according to step A are dissolved in 4.8 liters dry acetonitrile, 293.8 g (2.6 mols) N-methyl-4-piperidone are stirred in and then boiled under reflux for 24 hours. The reaction mixture is evaporated under a vacuum to such an extent that the residue still remains homogeneously liquid. The product is precipitated out by stirring in dichloromethane, filtered off with suction and washed with n-hexane. The mother liquor is evaporated to dryness, brought into solution by boiling with just a sufficient amount of dichloromethane and the product precipitated out by cooling, filtered off with suction and washed with n-hexane. The precipitated product fractions are thoroughly stirred with tert.-butyl methyl ether to such an extent that N-methyl-4-piperidone is no longer visible in the $^1$H-NMR spectrum of the product. The product is then so pure that, after thorough drying, it can be used for the cyclization in step C. Yield: 117.3 g (63.5% of theory).

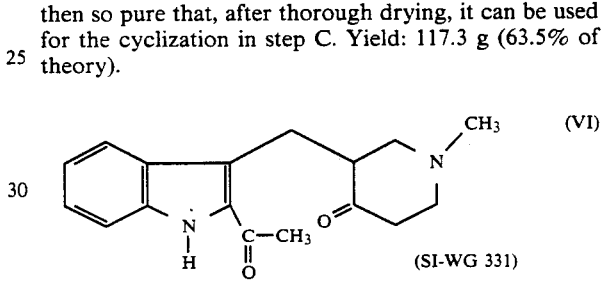

In the same way, and with the use of appropriate substituted precursors of the general formulae (III) and (IV), there were obtained the following compounds of general formula (Va)

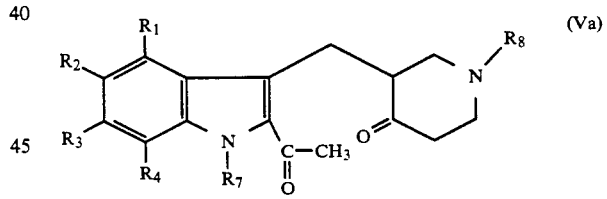

The compounds of general formula (Va) are summarized in Table 2.

Step C: Preparation of compounds of the formula Ia 1,3,4,5,7,12-Hexahydro-2-methyl-2H-pyrido [3',4':4,5]-cyclohept [1,2-b] indol-6-one

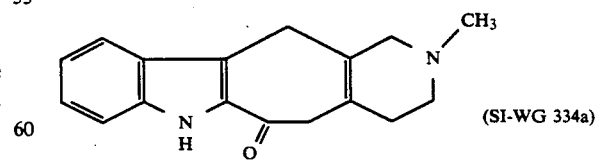

113.6 g (0.4 mol) of the compound obtained according to step C are dissolved in 5.3 liters absolute tetrahydrofuran under inert gas cover (nitrogen or argon) up to about 40° C., then cooled to 25° C. and 134.6 g (1.2 mols) potassium tert.-turylate stirred in. The reaction mixture is stirred for 30 minutes at 20°-25° C. and 12 liters saturated sodium chloride solution then added thereto. The resultant mixture is extracted three times with, in each case, 6.6 liters dichloromethane on an Ultra-Turrax. The combined dichloromethane phases are washed neutral with as little saturated sodium chloride solution as possible, dried over anhydrous sodium sulphate, filtered and evaporated to dryness on a rotary evaporator under a vacuum. The crude product is used immediately for the hydrogenation (Step D). Comparatively small amounts of double bond isomers in the crude product do not negatively influence the result of the hydrogenation. Yield 72.4 g (68% of theory).

In the same way and with the use of appropriately substituted compounds of general formula (V) from step B, there were obtained the following unsaturated compounds or general formula (Ia).

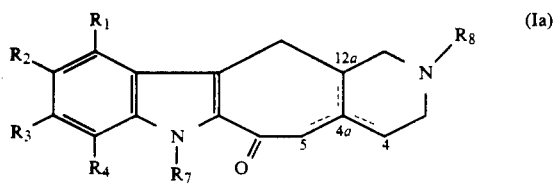

The compounds prepared and the material data thereof are summarized in Table 3.

Step D: Preparation of the title compound of (SI-WG 350)

1,3,4,4a,5,7,12,12a-Octahydro-2-methyl-2H-pyrido-[3',4':4,5] cyclohept [1,2-b] indol-6-one

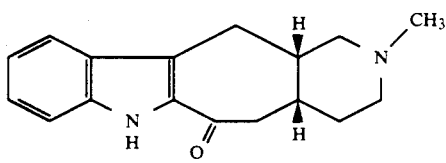

A hydrogenation vessel provided with a gassing stirrer is supplied under argon with 72 g palladium on active charcoal (5% Pd, dry) and a solution of 72 g (0.27 mol) of the substance obtained from step C added thereto in 3.5 liters pure tetrahydrofuran. Hydrogenation is carried out at normal pressure at 20°-25° C. up to the end of the take up of hydrogen (60–70 hours). The catalyst is filtered off and the filtrate evaporated to dryness under a vacuum in a rotary evaporator. After repeated crystallization from methanol, the pure title compound is obtained. Yield: 68 g (94% of theory). In the same way and with the use of appropriately substituted unsaturated compounds from step C, there were obtained the following compounds of general formula (Ia):

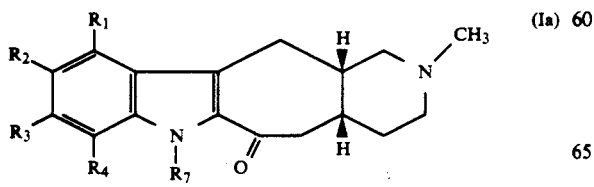

The compounds prepared and the material data thereof are summarized in Table 4.

EXAMPLE 2 a) Conversion of the compound obtained in step D of Example 1 (SI-WG 350) into the hydrochloride 14.5 g of the free phase are dissolved in 90 ml of methanol. After the addition of 5.22 ml of 32% aqueous hydrochloric acid, the product is precipitated out crystalline in quantitive yield by the gradual addition of diethyl ether.

The hydrochloride is filtered off with suction, washed with diethyl ether and dried under a vacuum at 40° C. The melting point of the pure compound is 299°–300° C.

b) Conversion of the compound obtained in step D of Example 1 SI-WG 350) into the hemitartrate:

1,073 mg (4 mmols) of SI-WG 350 were stirred into a solution of 300 mg (2 mmols) of L (+) tartaric acid in 15 ml of demineralized water, and the mixture was heated to 35° C. to form a clear solution. This solution was then filtered and freeze-dried. A pure white, amorphous salt was obtained.

EXAMPLE 3

Preparation of the compound 1,3,4,4a,5,6,7,12,12a-nonahydro-6-methoxy-2-methyl-2H-pyrido [3',4':4,5] cyclohept [1,2-b] indole

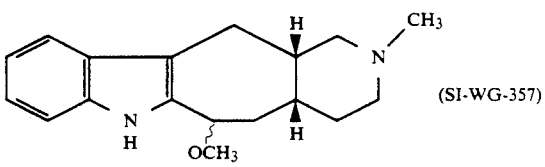

268 mg (1 mmol) of the compound SI-WG 350 obtained according to step D are dissolved in 200 ml methanol and stirred with 80 mg (about 2 mmol) sodium borohydride for 2 hours at room temperature with a magnetic stirrer. The batch is evaporated on a rotary evaporator to about 20 ml, mixed with 200 ml of water and exhaustively extracted with chloroform. The combined chloroform phases are dried over anhydrous sodium sulphate, filtered and evaporated to dryness under a vacuum. The product is purified chromatorgraphically on silica gel 60 with chloroform/methanol/water (59:33:8 v/v/v). Yield: 180 mg of amorphous substances (epimer mixture with regard to the methoxy group in the ratio of 4:1).

MS (m/e rel. Int. in %): 284 (M+k, 52%), 269 (100%), 252 (32%), 130 (25%), 109 (25%), 96 (68%)

IR (KBr, cm-1): 2920, 2843, 2782, 1452, 1337, 1988, 738

$^1$H-NMR (CDCl$_3$), δ ppm referred to TMS=0, the recognizable signals of the epimers with comparatively low amount are provided with a*): 1.47–3.17 (m, 12H), 2.25 and 2.31* (s,3H), 3.23* and 3.24 (s, 3H), 4.34* and 4.51 (dd, 1H), 7.00–7.57 (m, 4H), 8.21 and 8.42* (br.s., 1H) $^{13}$C-NMR (CDCl$_3$), δ ppm referred to TMS=0, signals of the epimer with the main part): 25.26 (t), 29.50 (t), 33.36 (d), 35.24 (t), 38.17 (d), 46.78 (q), 55.47 (t) 56.92 (q), 62.03 (t), 75.23 (d), 110.72(d), 112.82(s), 118.45 (d), 119.19 (d), 121.56 (d), 128.69 (s), 134.53(s), 135.62 (s).

EXAMPLE 4

Preparations of the compounds 1,3,4,7,12,12a-hexahydro-2-methyl-2H-pyrido
[3',4':4,5]-cyclohept [1,2-b] indol-6-one (SI-WG 359)

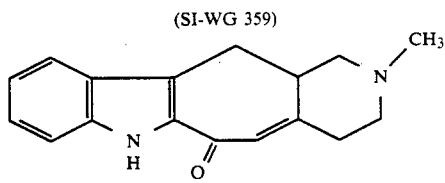

1,3,5,7,12,12a-hexahydro-2-methyl-2H-pyrido
[3',4':4,5]-cyclohept [1,2-b] indol-6-one (SI-WG 360)

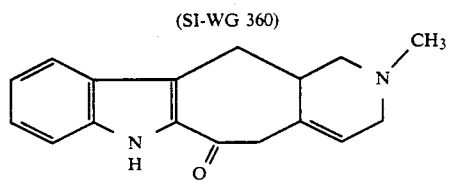

1,3,4,5,7,12-hexahydro-2-methyl-2H-pyrido
[3',4':4,5]-cyclohept [1,2-b] indol-6-one (SI-WG 334a)

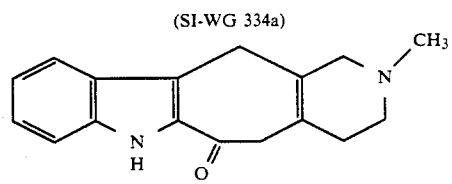

If, in step C of Example 1, as solvent there is used, instead of tetrahydrofuran, the same amount of 1,4-dioxan/N,N-dimethylformamide in a ratio of 2:1 under otherwise the same conditions, then there preponderantly results the compound SI-WG 360, besides the isomers SI-WG 334a and SI-WG 359. All three isomers can be separated by chromatography on silica gel 60. In the case of gradient elution with dichloromethane/methanol 93:7 to 70:30, there are obtained the compounds SI-WG 359, SI-WG 360 and SI-WG 334a in that sequence.

The material data of these compounds, as well as of the analogously prepared compound SI-WG 398 ($R_2$=Br), are summarized in Table 3.

EXAMPLE 5

Preparation of 1.3.4.4a,5,7,12, 12a-octahydro-10-hydroxy-2-methyl-2H-pyrido [3',4':4,5] cyclohept [1,2-b] indol-6-one (SI-WG 571)

The preparation is effected pursuant to the standard method (see, for example, M gerica, R bora and A brassie; helv kim acta 59 1976, 2551 to 2557 by demethylation of the corresponding methoxy compound.

0.4 g (1.34 mmols) of the compound SI-WG 449 obtained in analogy to step D of Example 1, was dissolved in 26.8 ml of dry dichloromethane. While stirring the solution at 0° C. with a magnetic stirrer, 2.68 ml of boron tribromide were added dropwise in at atmosphere of argon. After 5 minutes the mixture was heated to room temperature, and stirring was continued for 2.5 hours. Thereafter, while cooling the mixture on an icebath, a mixture of 26.8 ml of dichloromethane and 26.8 ml of methanol was added dropwise. The reaction mixture was then evaporated to dryness in a rotary evaporator, and the residue was taken up in methanol and again evaporated to dryness. The residue was then taken up in water, the solution was adjusted to pH 8.5 to 9 with ammonium hydroxide and was then extracted with chloroform. The chloroform phase was dried over anhydrous sodium sulphate and then evaporated to dryness. The residue was purified by chromatography on silica gel with $CH_2Cl_2$/methanol 1:1, and the purified fraction was crystallized from acetonitrile. Yield: 38.1 mg; MP: 266° to 268° C. In the same manner SI-WG 625 was prepared by demethylation of SI-WG 583.

TABLE 1

Compounds of the general formula (IIIa)

| compound substitution | empirical formula molecular weight | mp. °C. | IR KBr, (cm$^{-1}$) | $^1$H-NMR CDCl$_3$, δ(ppm ref to TMS = 0) |
|---|---|---|---|---|
| SI-WG 343 $R_2$ = H | $C_{13}H_{16}N_2O$ 216.282 | 171 | 3430, 3290, 3005, 1645, 1530, 1263, 749 | 2.37(s, 6H), 2.75(s, 3H), 3.93(s, 2H), 7.05-7.26(m, 1H), 7.26-7.49(m, 2H), 7.79(d, 1H), 9.52(br.s, 1H). |
| SI-WG 376 $R_2$ = CH$_3$ | $C_{14}H_{18}N_2O$ 230.309 | 154 | 3320, 2940, 2812, 2760, 1634, 1526, 1248, 799 | 2.28(s, 6H), 2.45(s, 3H), 2.80(s, 3H), 3.77(s, 2H), 7.15(dd, 1H), 7.41(br.d, 1H), 7.55(br.s, 1H), 9.13(br.s, 1H). |
| SI-WG 451 $R_2$ = HC—(CH$_3$)$_2$ | $C_{16}H_{22}N_2O$ 258.363 | 175 | 3312, 2943, 2810, 2758, 1630, 1522, 1247, 810 | 1.31(d, 6H), 2.28(s, 6H), 2.81(s, 3H), 3.02(h, 1H), 3.79(s, 2H), 7.16-7.41(m, 2H), 7.59(s, 1H), 9.08(br.s, 1H). |
| SI-WG 416 $R_2$ = F | $C_{13}H_{15}FN_2O$ 234.273 | 144 | 3322, 2965, 2933, 2862, 2822, 2772, 1640, 1526, 1256, 1184, 1168, 808, 722 | 2.27(s, 6H), 2.81(s, 3H), 3.75(s, 2H), 6.95-7.53(m, 3H), 9.18(br.s, 1H). |
| SI-WG 396 $R_2$ = Br | $C_{13}H_{15}BrNO_2$ 295.178 | 171 | 3315, 2972, 2938, 2815, 2764, 1638, 1527, 1253, 801 | 2.27(s, 6H), 2.81(s, 3H), 3.75(s, 2H), 7.27(dd, 1H), 7.40(dd, 1H), 7.95(br.d, 1H), 9.35(br.s, 1H). |
| SI-WG 446 $R_2$ = OCH$_3$ | $C_{14}H_{18}N_2O_2$ 246.308 | 160 | 3333, 2944, 2818, 2783, 2768, 1637, 1523, 1219 814 | 2.28(s, 6H), 2.79(s, 3H), 3.77(s, 2H), 3.87(s, 3H), 7.02(dd, 1H), 7.10-7.36(m, 2H), 9.16(br.s, 1H). |
| Compound Substituent $R_1R_2R_3R_4R_7$ | Empirical formula molecular weight | mp. °C. | IR KBr (cm$^{-1}$) *) Film | $^1$H-NMR CDCl$_3$, δ(ppm ref to TMS = 0) *) DM, SO-d$_6$ |

TABLE 1-continued

Compounds of the general formula (IIIa)

| Compound | Substituents | Empirical formula molecular weight | m.p. °C | IR KBr (cm$^{-1}$) | $^1$H-NMR CDCl$_3$, δ(ppm ref to TMS = 0) |
|---|---|---|---|---|---|
| SI-WG 574 | H, tert.Bu, H, H, H, | C$_{17}$H$_{24}$N$_2$O<br>272.393 | 187 | 3330, 2962, 2865, 2822, 2785, 1638, 1529, 1257, 820 | 1.39(s, 9H), 2.28(s, 6H), 2.81(s, 3H) 3.80(s, 2H), 7.35–7.50(m, 2H) 7.73(d, 1H), 9.10(br.s. 1H) |
| SI-WG 459 | H, Cl, H, H, H | C$_{13}$H$_{15}$ClN$_2$O<br>250.730 | 169 | 3308, 2922, 2848, 2807, 2760, 1634, 1517, 1443, 1418, 1250, 798, 722, 687 | 2.27(s, 6H), 2.81(s, 3H), 3.75(s, 2H) 7.20–7.39(m, 2H), 7.79(s, 1H) 9.30(br.s. 1H) |
| SI-WG 544 | H, O—CH$_2$—O, H, H | C$_{14}$H$_{16}$N$_2$O$_3$<br>260.295 | 194 | 3312, 2968, 2895, 2825, 2787, 1632, 1522, 1440, 1247, 952, 847 | 2.26(s, 6H), 2.74(s, 3H), 3.70(s, 2H) 5.97(s, 2H), 6.79(d, 1H), 7,11(d, 1H) 9.29(br.s, 1H) |
| SI-WG 556 | OCH$_3$, OCH$_3$, OCH$_3$, H, H, | C$_{16}$H$_{22}$N$_2$O$_4$<br>306.364 | 147 | 3321, 2933, 2852, 2817, 2772, 1614, 1568, 1513, 1263, 810 | 2.29(s, 6H), 2.78(s, 3H), 3.86(s, 3H) 3.90(s, 3H), 3.95(s, 2H), 4.07(s, 3H) 6.53(s, 1H), 8.97(br.s. 1H) |
| SI-WG 434 | H, OBz, H, H, H | C$_{20}$H$_{22}$N$_2$O$_2$<br>322.410 | 174 | 3330, 2933, 2855, 2816, 2785, 2757, 1631, 1522, 1457, 1218, 1200, 1018, 821, 740, 693 | 2.25(s, 6H), 2.78(s, 3H), 3.74(s, 2H) 5.12(s, 2H), 7.09(dd, 1H) |
| SI-WG 580 | H, H, H, OCH$_3$, H | C$_{14}$H$_{18}$N$_2$O$_2$<br>246.311 | 86 | 3328, 2967, 2938, 2850, 2808, 2757, 1660, 1574, 1532, 1258, 1230, 1018, 723 | 2.28(s, 6H), 2.79(s, 3H), 3.80(s, 2H) 3.95(s, 3H), 6.72(dd, 1H), 7.06(t, 1H) 7.37(dd, 1H), 9.28(br.s., 1H) |
| SI-WG 588 | H, H, H, H, CH$_3$ | C$_{14}$H$_{18}$N$_2$O<br>230.311 | 1 | *) 3048, 2940, 2857, 2813, 2764, 1657, 1510, 1463, 1402, 1369, 1238, 1033, 960, 742 | 2.24(s, 6H), 2.84(s, 3H), 3.77(s, 2H), 3.97(s, 3H), 7.06–7.40(m, 3H), 7.79(dt, 1H) |
| SI-WG 601 | H, NHAC, H. H. H | C$_{15}$H$_{19}$N$_3$O$_2$<br>273.337 | 208 | 3267, 3085, 2972, 2862, 2787, 1655, 1582, 1553, 1526, 1357, 1274, 1257, 1178, 999, 967, 869, 809, 756, 747, 605, 600 | *) 2.10(s, 3H), 2.22(s, 6H), 2.75(s. 3H) 3.81(s, 2H), 7.45(dd, 1H), 7.47(dd, 1H), 8.14(br.s, 1H), 10.01(s, 1H), 11.66(br.s, 1H) |
| SI-WG 597 | H, CN, H, H, H, | C$_{14}$H$_{15}$N$_3$O<br>241.295 | 178 | 3302, 3058, 2958, 2924, 2860, 2818, 2773, 2220, 1636, 1570, 1526, 1333, 1257, 1179, 1014, 978, 843, 812 | 2.28(s, 6H), 2.84(s, 3H), 3.82(s, 2H), 7.50(dd, 1H), 7.52(dd, 1H), 8.26(d, 1H) 9.62(br.s. 1H) |

TABLE 2

Compounds of the general formula (Va) sheet 2

| Compound Substituents | empirical formula molecular weight | m.p. °C | MS m/e (rel. Int. in %) | IR KBr (cm$^{-1}$) | $^1$H-NMR CDCl$_3$, δ(ppm ref to TMS = 0) |
|---|---|---|---|---|---|
| SI-WG 447<br>R$_2$ = OCH<br>R$_8$ = CH$_3$ | C$_{18}$H$_{22}$N$_2$O$_3$<br>314.383 | 142 | 314(M$^+$, 14), 296(2), 203(100), 188(40) 160(58), 125(72), 112(>100) | 3308, 2932, 2832, 2782, 1707, 1636, 1517, 1212, 801 | 2.13–3.29(m, 8H), 2.29(s, 3H), 2.64(s, 3H), 3.56(m, 1H), 3.87(s, 3H), 6.94–7.17(m, 2H), 7.28(d, 1H), 8.97(br.s, 1H) |
| SI-WG 420<br>R$_2$ = H<br>R$_8$ = H$_2$C—  | C$_{23}$H$_{24}$N$_2$O$_2$<br>360.455 | 170 | 360(M$^+$, 4), 342(2), 269(1), 201(62), 188 (>100), 173(54) 158(30), 146(60), 130(66), 112(100), 91 (>100) | 3325, 3022, 2913, 2820, 2793, 1709, 1648, 1532, 1260, 741, 696, 622 | 2.26–3.84(m, 11H), 2.65(s, 3H), 7.03–7.42(m, 8H), 3H), 1H), 9.00(br.s, 1H) |

| Compound | Substituents R$_1$, R$_2$, R$_3$, R$_4$, R$_7$, R$_8$ | Empirical formula molecular weight | mp. °C | MS m/e (rel. Int. in %) | IR KBr (cm$^{-1}$) | $^1$H-NMR CDCl$_3$, δ(ppm ref to TMS = 0) *) CO$_3$OD |
|---|---|---|---|---|---|---|
| SI-WG 452 | H, i-Pr, H, H, H, CH$_3$ | C$_{20}$H$_{26}$N$_2$O$_2$<br>326.642 | 124 | 326(M$^+$, 3), 215(37), 200(60), 172(26), 156(15), 125(60), 112(100) | 3325, 2955, 2778, 1715, 1650, 1533, 810, 647 | 1.30(d, 6H), 2.19–3.10(m, 8H) 2.28(s, 3H), 2.65(s, 3H), 3.23(br.d, 1H), 3.60(dd, 7.20(m, 2H), 7.46(s, 1H), 8.98(br.s, 1H) |
| SI-WG 575 | H, t.Bu, H, H, H, CH$_3$ | C$_{21}$H$_{28}$N$_2$O$_2$<br>340.469 | 164 | 340(M$^+$, 5), 228(42), 214(100, 187(33), 125(64), 116(100) | 3335, 2955, 2908, 2865, 2777, 1714, 1650, 1533, 1260, 819, 650 | 1.38(s, 9H), 2.12–3.10(m, 7H) 2.20(s, 3H), 2.64(s, 3H), 3.22(br.d, 1H), 3.62(dd,1H), 7.30(dd, 1H), 7.45(dd, 1H), 7.59(d, 1H), 8.97(br.s, 1H) |
| SI-WG 460 | H, Cl, H, H, H, CH$_3$ | C$_{17}$H$_{19}$ClN$_2$O$_2$<br>318.806 | 230 | 318/320(M$^+$, 6, 5/3), 218/220(18/18), 207/209(68/22), 192/190(42/14), 164/166(55/17), 125(>100), | 3300, 2943, 2922, 2895, 2844, 2780, 1704, 1644, 1526, 1258, 798, 638 | 2.16–3.06(m, 7H), 2.31(s, 3H), 2.67(s, 3H), 3.16(br.d, 1H), 3.56(dd, 1H), 7.30(m, 2H), 7.66(br.s, 1H), 9.00(br.s, 1H) |

TABLE 2-continued
Compounds of the general formula (Va) sheet 2

| | | | | | | |
|---|---|---|---|---|---|---|
| SI-WG 560 | H, O—CH$_2$O, H, H, CH$_3$ | C$_{18}$H$_{20}$N$_2$O$_4$ 328.371 | 190 | 112(>100), 328(M$^+$, 10), 310(2), 241(9), 227(19), 216(>100), 202(90), 174(>100), 116(>100) | 3303, 2945, 2930, 2890, 2850, 2795, 1696, 1628, 1527, 1470, 1442, 1252, 1037, 947, 831, 618 | 2.14-3.24(m, 7H), 2.29(s, 3 2.58(s, 3H), 3.42(br.d, 1H), 3.64(br.d, 1H), 5.98(d, 2H), 6.76(d, 1H), 6.97(br.s, 1H), 9.07(br.s, 1H) |
| SI-WG 531 | H, H, H, H, H, n-Pr | C$_{19}$H$_{24}$N$_2$O$_2$ 312.415 | 164 | 312(M$^+$, 0.7), 283(2) 198(9), 184(4), 173(11), 140(100) 130(12), 124(9), 110(3) | 3320, 2957, 2932, 2903, 2875, 2775, 1713, 1647, 1533, 1262, 741 | 0.85(t, 3H), 1.34(m, 2H), 2.17-3.13(m, 7H), 2.31(t, 2H) 2.66(s, 3H), 3.18(d, 1H), 3.65(br.d, 1H), 7.13(m, 1H), 7.38(m, 2H), 7.67(d, 1H), 8.96(br.s, 1H) |
| SI-WG 581 | H, H, H, OCH$_3$, H, CH$_3$ | C$_{18}$H$_{22}$N$_2$O$_3$ 314.387 | 124 | 314(M$^+$, 5), 203(41) 188(11), 160(14), 145(4), 125(24), 112(100) | 3306, 3003, 2954, 2852, 2884, 1714, 1664, 1642, 1574, 1536, | 2.12-3.09(m, 7H), 2.27(s, 3H), 2.64(s, 3H), 3.17(d, 1H), 3.60 (d, 1H), 3.96(s, 3H), 6.73 (dd, 1H), 7.05(t, 1H), 7.25 (d, 1H), 9.09(br.s, 1H) |
| SI-WG 557 | OCH$_3$, OCH$_3$, OCH$_3$, H, H, CH$_3$ | C$_{16}$H$_{22}$N$_2$O$_4$ 374.440 | 159 | 374(M$^+$, 9), 263(100) 248(57), 220(26), 205(8), 125(15), 112(66) | 3315, 2940, 2846, 2788, 1695, 1654, 1622, 1567, 1516, 1257, 1104, 804 | 2.15-3.30(m, 8H), 2.29(s, 3H), 2.62(s, 3H), 3.68(d, 1H), 3.84 (s, 3H), 3.90(s, 3H), 4.01 (s, 3H), 6.51(s, 1H), 8.93 (s, 1H) |
| SI-WG 602 | H, NHAc, H, H, H, CH$_3$ | C$_{19}$H$_{23}$N$_3$O$_3$ 341.413 | 205 | 323(M$^+$-18, 100), 308(15), 294(22), 280(46), 252(22), 209(15), 141(8), 122(8), 108(24), 96(46) | 3328, 3294, 2968, 2937, 2842, 2786, 1709, 1653, 1633, 1542, 1522, 1263, 1140, 970, 811, 712, 672 | *)2.13-3.46(m, 8H), 2.14(s, 3H) 2.26(s, 3H), 2.58(s, 3H), 3.57 (br.d, 1H), 7.37(d, 1H), 7.38 (d, 1H), 7.92(t, 1H) |
| SI-WG 598 | H CN, H, H, H, CH$_3$ | C$_{18}$H$_{19}$N$_3$O$_2$ 309.371 | 234 | 309(+, 1), 291(2), 209(5), 198(8), 183(5), 155(8), 140(3), 124(18), 112(100) | 3293, 2968, 2928, 2860, 2797, 2778, 2227, 1703, 1650, 1533, 1267, 1063, 887, 811 | 2.12-3.57(m, 8H), 2.32(s, 3H), 2.70(s, 3H), 3.63(dd, 1H), 7.47(dd, 1H), 7.55(dd, 1H), 8.11(t, 1H), 9.42(br.s, 1H) |

TABLE 3
Unsaturated compounds of the general formula (Ia) (sheet 1)

| compound substituents | empirical formula molecular weight | position of double bond | prepa. acc example | MS m/e (rel. Int. in %) | IR KBr (cm$^{-1}$) | $^1$H-NMR (CDCl$_3$) δ(ppm ref to TMS = 0) | $^{13}$C-NMR (CDCl$_3$) δ(ppm ref to TMS = 0) |
|---|---|---|---|---|---|---|---|
| SI-WG 334a R$_2$ = H R$_8$ = CH$_3$ | C$_{17}$H$_{18}$N$_2$O 266.342 | 4a-12a | 1-c | 266(M$^+$, 100) 251(11), 237 (8), 223(18), 194(26), 180 (14), 167(7), 154(5), 129 (8), 109(16), 96(26) | 3298, 2925 2893, 1634 1529, 1460 1336, 1258 740 | 2.36(s, 3H), 2.36 (t, 2H)2.48(t, 2H) 3.06(s, 2H), 3.44 (s, 2H), 3.57(s, 2H) 7.15(td, 1H), 7.28- 7.58(m, 2H), 7.68 (d, 1H), 8.18 (br.s, 1H) | 28.26(t), 31.69(t), 45.24(q), 48.64(t), 51.93(t), 59.22(t), 112.14(d), 120.31(d) 120.48(d), 124.96(s) 125.22(s), 126.47(d) 126.98(s), 132.27(s) 134.01(s), 135.79(s) 188.22(s) |
| SI-WG 359 R$_2$ = H R$_8$ = CH$_3$ | C$_{17}$H$_{18}$N$_2$O 266.342 | 4a-4 | | 266(M$^+$, 100) 251(9), 237 (6), 223(55), 206(6), 195 (25), 180(17), 167(13), 108 (15), 96(20 | 3282, 2932 2780, 1632 1577, 1458 1327, 739 | 2.05-2.56(-m, 9H) 2.37(s, 3H), 6.28 (s, 1H), 7.03-7.49 (m, 3H), 7.64(d, 1H) 9.73(br.s, 1H) | 27.11(t), 37.23(t), 39.88(d), 45.52(q), 54.82(t), 61.96(t), 112.20(d), 120.05(d) 120.26(s), 120.66(d) 126.09(s), 126.68(s) 128.49(d), 133.78(s) 136.92(s), 157.13(s) 182.41(s) |
| SI-WG 360 R$_2$ = H R$_8$ = CH$_3$ | C$_{17}$H$_{18}$N$_2$O 266.342 | 4a-4 | 4 | 266(M$^+$, 100) 251(7), 238 (16), 223(41) 206(10), 195 (77), 180(46) 167(50), 108 (30), 94(27) | 3398, 2927 2775, 1637 1528, 1456 1327, 1242 741 | 2.07(dd, 1H), 2.33 (s, 3H), 2.54-3.40 (m, 6H) 3.48(s, 2H) 5.66(br.s, 1H), 7.06-7.22(m, 1H), 7.33-7.45(m, 2H), 7.68(d, 1H), 9.20(br.s, 1H) | 26.50(t), 37.91(d), 45.43(q), 48.74(t), 54.59(t), 57.75(t), 121.11(d), 120.23(d) 120.70(d), 122.68(s) 125.01(d), 126.53(d) 127.97(s), 131.58(s) 132.26(s), 136.70(s) 190.12(s) |
| SI-WG 378 | C$_{18}$H$_{20}$N$_2$O | 4a-12a | 1-c | | | 2.19-2.63(m, 4H), 2.35 | |

TABLE 3-continued

Unsaturated compounds of the general formula (1a) (sheet 1)

| Compound | Substituents | Empirical formula molecular weight | position double bond | mfg. accord to example | MS m/e (rel. Int. in %) | IR KBr (cm⁻¹) | ¹H-NMR (CDCl₃) bzw. *) CD₃OD δ(ppm ref to TMS = 0) | ¹³C-NMR (CDCl₃) bzw. *) CD₃OD δ(ppm ref to TMS = 0) |
|---|---|---|---|---|---|---|---|---|
| | $R_2 = CH_3$ $R_8 = CH_3$ | 280.369 | | | | | (s, 3H), 2.54(s, 3H) 3.04(s, 2H), 3.42 (s, 2H), 3.53(s, 2H), 7.15(d, 1H), 7.29 (d, 1H), 7.44(s, 1H) 9.14(br.s. 1H) | |
| SI-WG 418 | $R_2 = F$ $R_8 = CH_3$ | $C_{17}H_{17}FN_2O$ 284.333 | 4a–12a | 1-c | 284($M^+$, 100), 269(8), 255 (6), 241(18), 213(26), 198 (15), 185(10) 108(16), 96(21) | 3297, 2928 2897, 1646 1530, 1468 802 | 2.20–2.62(m, 4H), 2.36 (s, 3H), 3.05(s, 2H), 3.45(s, 2H), 3.48 (s, 2H), 6.95–7.43 (m, 3H), 9.20(br.s. 1H) | |
| SI-WG 398 | $R_2 = Br$ $R_8 = CH_3$ | $C_{17}H_{17}BrN_2O$ 345.238 | 4a–4 | 4 | 344/346($M^+$, 100), 329/331 (15), 316/318 (21), 301/303 (42), 273/275 (66), 258/260 (26), 245/247 (28), 193(48), 167(29), 108 (71), 94(76) | 3300, 2932 2774, 1629 1522, 1449 1252, 797, 677 | 1.96(dd, 1H), 2.32 (s, 3H), 2.47–3.37 (m, 6H), 3.48(s, 2H), 5.67(br.s, 1H), 7.27 (dd, 1H), 7.42(dd, 1H) 7.81(d, 1H), 9.05 (br.s, 1H) | 26.74(t), 38.06(d), 45.60(q), 48.84(t), 54.81(t), 57.94(t), 113.41(s), 113.64(d) 121.89(s), 123.33(d) 125.87(s), 129.39(d) 129.68(s), 131.03(s) 133.10(s), 135.10(s) 190.20(s) |
| SI-WG 448 | $R_2 = OCH_3$ $R_8 = CH_3$ | $C_{18}H_{20}N_2O_2$ 296.368 | 4a–12a | 1-c | 296($M^+$, 100), 281(19), 267 (13), 253(35) 225(43), 210 (25), 159(26) 108(29), 96(56) | 3440, 2932 2807, 1628 1525, 1465 1437, 1213 799 | 2.28–2.40(m, 2H), 2.37(s, 3H), 2.50 (t, 2H), 3.08(s, 2H) 3.43(s, 2H), 3.53 (s, 2H), 3.88(s, 3H) 6.98–7.06(m, 2H), 7.27–7.34(m, 1H), 8.89(br.s, 1H) | |
| SI-WG 421 | $R_2 = H$ $R_8 = H_2C-$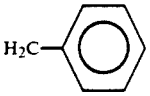 | $C_{23}H_{22}N_2O$ 342.4396 | 4a–12a | 1-c | 342($M^+$, 72) 327(6), 313 (4), 299(3), 251(12), 223 (15), 194(21) 172(42), 146 (12), 120(7) 91(100) | 3305, 2882 2800, 2757 1633, 1528 1454, 741, 694 | 2.33(m, 2H), 2.52 (t, 2H), 3.09(s, 2H) 3.43(s, 2H), 3.54 (s, 2H), 3.54 (s, 2H), 3.58(s, 2H) 7.05–7.47(m, 8H), 7.67(d, 1H), 8.98 (br.s, 1H) | 28.35(t), 31.63(t), 48.74(t), 49.71(t), 57.50(t), 62.40(t), 112.21(d), 120.27(d) 120.53(d), 125.18(s) 125.33(s), 126.46(d) 126.88(s), 127.18(d) 128.31(d, 2C), 129.20 (d, 2C), 132.00(s) 134.09(s), 135.75(s) 137.97(s), 188.37(s) |
| Compound | Substituents $R_1R_2R_3R_4R_7R_8$ | Empirical formula molecular weight | position double bond | mfg. accord to example | MS m/e (rel. Int. in %) | IR KBr (cm⁻¹) | ¹H-NMR (CDCl₃) bzw. *) CD₃OD δ(ppm ref to TMS = 0) | ¹³C-NMR (CDCl₃) bzw. *) CD₃OD δ(ppm ref to TMS = 0) |
| SI-WG 453 | H, i-Pr, H, H, H, CH₃ | $C_{20}H_{24}N_2O$ 308.426 | 4a–12a | 1-C | | 3308, 2957, 2788, 1648, 1536, 1464, 1342, 1258, 812 | 1.31(d, 6H), 2.31–2.47(m, 4H), 2.36(s, 3H) 2.95(n, 1H), 3.02(s, 2H), 3.42(s, 2H), 3.56(s, 2H), 7.28(m, 2H), 7.48(s, 1H), 8.97(br.s, 1H) | |
| SI-WG 576 | H, t-Bu, H, H, H, CH₃ | $C_{21}H_{26}N_2O$ 322.453 | 4a–12a | 1-c | 322($M^+$, 9) 308(2), 235, (3), 223(10), 202(21) 153(5), 144 (14), 128 (34), 109 (100) | 3310, 2960, 2907, 2872, 2845, 2788, 2740, 1650, 1536, 1462, 1256, 1242, 812 | 1.40(s, 9H) 2.39–2.75(m, 4H) 2.41(s, 3H), 3.16(s, 2H), 3.43(s, 2H), 3.58(s, 2H) 7.36–7.51(m, 2H) 7.60(s, 1H) 8.99(br.s, 1H) | 28.21(t), 31.31(t), 31.72(3xq), 34.75(s), 45.01(q), 48.60(t), 51.81(t), 58.93(t); 111.79(d), 115.58(d), 125.11(s), 125.21(s), 125.47(d), 126.66(s), 132.48(s), 133.56(s), 134.14(s), 143.38(s), 188.06(s) |
| SI-WG 461 | H, Cl, H, H, H, CH₃ | $C_{17}H_{17}ClN_2O$ 300.790 | 4a–4 | 4 | 300/302 ($M^+$, 100/33), 285/287(12/4), 271/273(11/4), 257/259 (29/10), 229/231 (43/15), 214(19), 193(18), 108(35), 95(57) | 3313, 2966, 2938, 2865, 2837, 2783, 2767, 2733, 1634, 1528, 1458, 1256, 802, 752, 683 | 2.03(dd, 1H), 2.31(s, 3H), 2.36–3.35(m, 6H), 3.48(s, 2H), 5.67(br.s, 1H), 7.31(dd, 2H), 7.65(s, 1H), 9.15(br.s, 1H) | 26.79(t), 38.09(d), 45.59(q), 48.84(t), 54.82(t), 57.94(t), 113.25(d), 120.11(d), 122.01(s), 125.84(d), 126.00(s), 126.91(d), 129.01(s), 131.03(s), 133.25(s), 134.86(s), 190.20(s) |
| SI-WG 561 | H, O—CH₂O, H, H, CH₃ | $C_{18}H_{18}N_2O_3$ 310.355 | 4a–12a | 1-C | 310($M^+$, 100), 295(12), 282 | 3275, 2920, 2888, 2852, | 2.21–2.60(m, 4H), 2.35(s, 3H), | |

TABLE 3-continued

Unsaturated compounds of the general formula (Ia) (sheet 1)

| | | | | | | |
|---|---|---|---|---|---|---|
| | | | | (13), 267(37), 239(37), 224 (13), 203(10), 188(12), 173 (16), 108(27), 96(48) | 2780, 1624, 1527, 1467, 1275, 1248, 1196, 1031, 943 | 3.03(s, 2H), 3.39(s, 2H), 3.45(s, 2H), 5.98(s, 2H), 6.78(s, 1H), 6.97(s, 1H), 8.99(br.s, 1H) | |
| SI-WG 582 | H, H, H, OCH$_3$, H, CH$_3$ | C$_{18}$H$_{20}$N$_2$O$_2$ 296.372 | 4a-12a | 296(M$^+$, 100), 281(13), 267 (10), 225(28), 210 (16), 188(7), 159(11), 148 (7), 134(9), 122(9), 109 (15), 96(29) | 3308, 3060, 2934, 2840, 253(38), 2782, 1649, 1573, 1389, 1331, 1257, 1093, 967, 782, 730 | 2.23-2.61(m, 4H), 2.35(s, 3H), 3.42(s, 2H), 3.54(s, 2H), 3.95(s, 3H), 6.73(dd, 1H), 7.06(t, 1H), 7.26(d, 1H), 9.08(br.s, 1H) | 3.04(s, 2H), |
| SI-WG 558 | OCH$_3$, OCH$_3$, OCH$_3$H, H, CH$_3$ | C$_{20}$H$_{24}$N$_2$O$_4$ 356.425 | 4a-12a | 356(M$^+$, 100), 341(15), 325 (9), 313(34), 298(221), 285 (17), 270(10), 170(4), 141 (6), 122(7), 108(12), 96 (29) | 3290, 2947, 2878, 2832, 2768, 1637, 1567, 1518, 1456, 1379, 1275, 1111, 1067, 999, 809, 688 | 2.20-2.56(m, 4H) 2.36(s, 3H), 3.06(s, 2H), 3.39(s, 2H), 3.83(s, 3H), 3.87(s, 3H), 3.90(s, 3H), 4.05(s, 3H), 6.55(s, 1H), 9.03(s, 1H) | 28.92(t), 31.69(t), 45.35(q), 48.41(t), 52.05(t), 56.11(q), 59.33(t), 61.23(q), 61.42(q), 89.36(d), 114.70(s), 125.01(s), 126.39(s), 131.60(s), 133.48(s), 134.73(s), 137.10(s), 148.54(s), 154.79(s), 187.45(s) |
| SI-WG 603 | H, NHAC, H, H, H, CH$_3$ | C$_{19}$H$_{21}$N$_3$O$_2$ 323.398 | 4a-12a | 323(M$^-$, 100), 308(13), 294 (9), 280(31), 252(18), 238 (10), 209(10), 195(5), 186 (5), 140(5), 122(5), 108 (15), 96(22) | 3292, 2933, 2893, 2835, 2777, 1637, 1529, 1482, 1462, 1437, 1369, 1252, 803, 702, 678 | *)2.15(s, 3H), 2.23-2.65(m, 4H) 2.32(s, 3H), 3.06(s, 2H), 3.31(s, 2H), 3.57(s, 2H), 7.30(d, 1H), 7.31(d, 1H), 8.02(br.s, 1H) | |
| SI-WG 599 | H, CN, H, H, H, CH$_3$ | C$_{18}$H$_{17}$N$_3$O 291.355 | 4a-4 | 291(M$^+$, 100), 276(8), 262 (6), 248(14), 220(23), 205 (14), 192(10), 122(4), 108 (12), 96(18) | 3287, 2962, 2936, 2865, 2833, 2782, 2760, 2726, 2217, 1632, 1531, 1461, 1259, 1143, 979, 810, 687 | 2.07(dd, 1H), 2.33(s, 3H), 2.36(m, 1H), 2.77(m, 2H), 3.06(m, 2H), 3.26(m, 2H), 3.51(s, 2H), 5.69(s, 1H), 7.48(dd, 1H), 7.54(dd, 1H), 8.07(t, 1H), 9.23(br.s, 1H) | |
| Si-WG 532 | H, H, H, H, H, n-PR | C$_{19}$H$_{22}$N$_2$O 294.399 | 4a-12a | | 3306, 3054, 2958, 2930, 2875, 2810, 2768, 2728, 1637, 1572, 1533, 1460, 1330, 1238, 743 | 0.91(t, 3H), 1.55(m, 2H), 2.25-2.50(m, 6H), 3.09(s, 2H), 3.44(s, 2H), 3.57(s, 2H), 7.06-7.44(m, 3H), 7.70(d, 1H), 9.07(br.s, 1H) | 11.99(q), 20.38(t), 28.41(t), 31.74(t), 48.71(t), 50.05(t), 57.74(t), 60.11(t), 112.18(d), 120.30(d), 120.53(d), 125.19(s), 126.48(d), 126.52(d), 127.01(s), 132.30(s), 134.15(s), 135.82(s), 188.38(s) |

TABLE 4

Saturated compounds of the general formula (Ia)

| Compound Substituent | empirical formula molecular weight highly resolved | m.p. °C. | MS $m/e$ (rel. Int. in %) | IR KBr (cm$^{-1}$) | $^1$H-NMR (CDCl$_3$) $\sigma$(ppm ref to TMS = 0) | $^{13}$C-NMR $\sigma$(ppm ref to TMS = 0) |
|---|---|---|---|---|---|---|
| SI-WG 350 R$_2$ = H | C$_{17}$H$_{20}$N$_2$O 268.358 | 184 | 268(M$^+$, 67), 130(19), 110(47), 96(100) | 2922, 2800, 1660, 1569, 1532, 1465, 1447, 739 | 1.70-1.95(m, 2H), 2.04-2.28(m, 2H), 2.32(s, 3H), 2.32-2.48(m, 3H), 2.54-2.64(m, 2H), 2.76-2.94(m, 2H), 3.26(dd, 1H), 7.12-7.19(m, 1H), 7.30-7.41(m, 2H), 7.70(d, 1H), 9.00(s, 1H) | 26.24(t), 30.94(t), 31.98(d), 37.57(d), 45.60(t), 46.39(q), 53.78(t), 60.61(t), 112.09(d), 120.26(d), 120.88(d), 124.81(s), 126.45(d), 127.32(s), 133.16(s), 136.43(s), 193.45(s). |
| SI-WG 379 R$_2$ = CH$_3$ | C$_{18}$H$_{22}$N$_2$O 282.384 | 210 | 282(M$^+$, 29), 144(21), 110(39), | 3308, 2934, 2783, 1634, 1531, 1468, | 1.63-1.96(m, 2H), 1.96-3.00(m, 9H), 2.31(s, 3H), | 21.45(q), 26.35(t), 31.33(t), 32.24(d), 37.90(d), 45.76(t), |

TABLE 4-continued

| Compound | Substituents | empirical formula molecular weight | mp. °C. | MS $m/e$(rel. Int. in %) | IR KBr (cm$^{-1}$) | $^1$H-NMR CDCl$_3$, σ (ppm ref a. TMS = 0) *)CD$_3$OD | $^{13}$C-NMR CDCl$_3$, σ (ppm ref to TMS = 0) |
|---|---|---|---|---|---|---|---|
| | | | | 96(100) | 1447, 799 | 2.45(s, 3H), 3.24(dd, 1H), 7.16(dd, 1H), 7.29(d, 1H), 7.47(br.s, 1H), 8.79(br.s, 1H) | 46.67(q), 53.97(t), 61.04(t), 111.78(d), 120.13(d), 124.55(s), 127.59(s), 128.40(d), 129.53(s), 133.22(s), 134.88(s), 193.61(s) |
| SI-WG 419 R$_2$ = F | | C$_{17}$H$_{19}$FN$_2$O 286.348 | 200 | 286(M$^+$, 78) 148(14), 110(51), 96(100) | 3295, 2915, 2800, 1662, 1525, 1471, 794 | 1.54–1.98(m, 3H), 1.98–3.00(m, 8H), 2.32(s, 3H), 3.16(dd, 1H), 6.95–7.52(m, 3H), 9.15(br.s, 1H) | 26.45(t), 31.20(t), 32.24(d), 37.97(d), 45.91(t), 46.70(q), 54.06(t), 61.07(t), 105.24(dd), 113.15(dd), 115.47(dd), 125.00(d), 127.50(d), 133.00(s), 134.50(s), 157.50(d), 193.71(s). |
| SI-WG 399 R$_2$ = Br | | C$_{17}$H$_{19}$BrN$_2$O 347.2538 | 243 | 346/348(M$^+$, 17) 208/210(3), 110(44), 96(100) | 3300, 2930, 2797, 1633, 1529, 1460, 799 | 1.63–1.98(m, 2H), 1.98–2.96(m, 9H), 2.32(s, 3H), 3.18(dd, 1H), 7.30(d, 1H), 7.42(dd, 1H), 7.85(d, 1H), 9.01(br.s, 1H) | 26.31(t), 31.16(t), 32.25(d), 38.00(d), 45.89(t), 46.68(q), 54.04(t), 61.06(t), 113.25(s), 113.59(d), 123.53(d), 124.15(s), 128.95(s), 129.27(d), 133.95(s), 134.00(s), 193.75(s). |
| SI-WG 449 R$_2$ = OCH$_3$ | | C$_{18}$H$_{22}$N$_2$O$_2$ 298.384 | 216 | 298(M$^+$, 62), 160(21), 110(52), 96(100) | 3288, 2922, 2775, 1626, 1523, 1464, 1211, 803 | 1.58–1.97(m, 2H), 1.97–3.03(m, 9H), 2.32(s, 3H), 3.21(dd, 1H), 3.88(s, 3H), 6.96–7.16(m, 2H), 7.29(dd, 1H), 8.81(br.s, 1H) | 26.49(t), 31.25(t), 32.32(d), 37.99(d), 45.85(t), 46.73(q), 54.11(t), 55.78(q), 61.18(t), 100.94(d), 113.07(d), 118.14(d), 124.44(s), 127.61(s), 131.81(s), 133.68(s), 154.50(s), 193.47(s). |

| Compound | Substituents R$_1$, R$_2$, R$_3$, R$_4$, R$_7$, R$_8$ | empirical formula molecular weight | mp. °C. | Mfg. accord. to Example | MS $m/e$(rel. Int. in %) | IR KBr (cm$^{-1}$) | $^1$H-NMR CDCl$_3$, σ (ppm ref a. TMS = 0) *)CD$_3$OD | $^{13}$C-NMR CDCl$_3$, σ (ppm ref to TMS = 0) |
|---|---|---|---|---|---|---|---|---|
| SI-WG 454 | H, i-Pr, H, H, H, CH$_3$ | C$_{20}$H$_{26}$N$_2$O 310.442 | 180 | 1-D | 310(M$^+$, 12) 172(9), 110(36), 96(100) | 2958, 2923, 2892, 2800, 1652, 1530, 1466, 1447, 1344, 801 | 1.31(d, 6H), 1.68–1.93(m, 2H), 1.98–3.13(m, 9H), 2.32 (s, 3H), 3.27 (dd, 1H), 7.27 (dd, 1H), 7.32 (d, 1H), 7.51 (br.s, 1H), 8.98 (br.s, 1H) | 24.42(q), 24.48 (q), 26.39(t), 31.34(t), 32.30 (d), 34.23(d), 37.88(d), 45.81 (t), 46.73(q), 54.03(t), 61.09 (t), 111.97(d), 117.31(d), 124.89 (s), 126.20(d), 127.43(s), 133.30 (s), 135.19(s), 140.98(s), 193.68(s) |
| SI-WG 578 | H, t-Bu, H, H, H, CH$_3$ | C$_{21}$H$_{28}$N$_2$O 324.469 | 220 | 1-D | 324(M$^+$, 41) 252(7), 186(14), 110(38), 96(100) | 3285, 2953, 2862, 2778, 1630, 1532, 1461, 1447, 811 | 1.39(s, 9H), 1.66–1.95(m, 2H), 1.97–3.04(m, 9H), 2.36 (s, 3H), 3.24 (dd, 1H), 7.35–7.56 (m, 2H), 7.63 (br.s, 1H), 8.93 (br.s, 1H) | 26.35(t), 31.22 (t), 31.72(3xq), 32.27(d), 34.74 (s), 37.88(d), 45.82(t), 46.67 (q), 54.05(t), 61.04(t), 111.70 (d), 116.10(d), 125.16(s), 125.33 (d), 127.10(s), 133.31(s), 134.73 (s), 143.29(s), 193.55(s) |
| SI-WG 462 | H, Cl, H, H, H, CH$_3$ | C$_{17}$H$_{19}$ClN$_2$O 302.806 | 208 | 1-D | 302/304 (M$^+$,33/11) 164/162 (15/10), 110(52), 96(100) | 3304, 2933, 2847, 2793, 2780, 1631, 1528, 1458, 800 | 1.64–1.99(m, 2H), 2.00–3.04(m, 9H), 2.32(s, 3H), 3.18 (dd, 1H), 7.29 (d, 1H), 7.30 (d, 1H), 7.66 (s, 1H), 9.01 (br.s, 1H) | 26.32(t), 31.16 (t), 32.24(d), 37.94(d), 45.89 (t), 46.65(q), 54.02(t), 61.02 (t), 133.29(d), 120.27(d), 124.30 (s), 125.99(s), 126.79(d), 128.39 (s)134.09(s), 134.67(s), 193.67(s) |
| SI-WG 562 | H, O—CH$_2$O, H, H, CH$_3$ | C$_{18}$H$_{20}$N$_2$O$_3$ 312.371 | 223 | 1-D | 312(M$^+$, 37) 174(19), 110(27), 96(100) | 3280, 2915, 2842, 2778, 1617, 1523, 1463, 1277, 1258, 1196, 1033, 948 | 1.71–1.96(m, 2H), 1.96–2.96(m, 9H), 2.31(s, 3H), 3.11 (dd, 1H), 5.97 (s, 2H), 6.80 (d, 1H), 6.98 (s, 1H), 9.12 | 26.62(t), 31.34 (t), 32.33(d), 37.81(d), 45.51 (t), 46.70(q), 54.01(t), 61.06 (t), 91.91(d), 98.16(d), 101.12 |

TABLE 4-continued

| | | | | | | | | |
|---|---|---|---|---|---|---|---|---|
| | | | | | | | (br.s, 1H) | (t), 121.62(s), 125.53(s), 132.48 (s), 132.80(s), 143.93(s), 148.78 (s), 192.42(s) |
| SI-WG 583 | H, H, H, OCH₃, H, CH₃ | C₁₈H₂₂N₂O₂ 298.388 | 155 | 1-D | 298(M⁺, 93) 253(8), 227(8), 160(20), 110(47), 96(100) | 3054, 2908, 2839, 2785, 1654, 1573, 1460, 1396, 1327, 1252, 1090, 724 | 1.63-1.94(m, 2H), 1.94-3.03(m, 9H), 2.31(s, 3H), 3.23 (dd, 1H), 6.73 (dd, 1H), 7.06 (t, 1H), 7.28 (d, 1H), 9.01 (br.s, 1H) | 26.59(t), 31.30 (t), 32.16(d), 37.91(d), 45.78 (t)46.69(q), 53.99(t), 55.45 (q), 61.04(t), 105.03(d), 113.07 (d), 120.64(d), 125.18(s), 127.64 (s), 128.53(s), 132.79(s), 146.69 (s), 193.45(s) |
| SI-WG 587 | OCH₃, OCH₃, OCH₃, H, H, CH₃ | C₂₀H₂₆N₂O₄ 358.441 | 208 | 1-D | 358(M⁺, 511) 300(10), 286(10), 220(18), 205(8), 110(38), 96(100) | 3275, 2935, 2837, 2786, 1614, 1567, 1522, 1456, 1279, 1253, 1118, 1104, 1070, 1000, 922, 813 | 1.63-1.97(m, 2H), 1.97-3.00(m, 9H), 2.36(s, 3H), 3.74 (dd, 1H), 3.87 (s, 3H), 3.90 (s, 3H), 4.02 (s, 3H), 6.55(s, 1H) 8.99(br.s, 1H) | 27.07(t), 31.55 (t), 31.93(d), 38.24(d), 45.44 (t), 46.71(q), 53.92(t), 56.13 (q), 60.99(t), 61.40(2xq), 89.34 (d), 115.05(s), 126.29(s), 132.57 (s), 134.08(s), 137.16(s), 148.78 (s), 154.73(s), 192.73(s) |
| SI-WG 571 | H, OH, H, H, H, CH₃ | C₁₇H₂₀N₂O₂ 284.361 | 268 | 5 | 284(M⁺, 64) 239(5), 213(6), 146(17), 110(42), 96(100) | 3332, 2942, 2921, 2807, 1632, 1527, 1467, 1450, 1240, 1213, 1151, 1109, 824, 792 | *)1.65-1.98(m, 2H) 1.98-2.99(m, 9H), 2.33(s, 3H), 3.11 (dd, 1H), 6.87 (dd, 1H), 6.99 (dd, 1H), 7.24 (dd, 1H) | |
| SI-WG 625 | H, H, H, OH, H, CH₃ | C₁₇H₂₀N₂O₂ 284.361 | 233 | 5 | 284(M⁺, 60) 239(5), 213(6), 146(17), 110(47), 96(100) | 3320, 3058, 2935, 2853, 2788, 1652, 1632, 1452, 1383, 1308, 1266, 786, 734 | 1.63-1.95(m, 2H), 1.95-3.04(m, 9H), 2.33(s, 3H), 3.26 (dd, 1H), 6.92 (td, 1H), 7.09 (d, 1H), 7.23 (dd, 1H), 11.04 (s, 1H) | |
| SI-WG 604 | H, NHAc, H, H, H, CH₃ | C₁₉H₂₃N₃O₂ 325.414 | 152 | 1-D | 325(M⁺, 49) 297(8), 283(6), 254(6), 187(14), 110(49), 96(100) | 3280, 2924, 2847, 2793, 1652, 1588, 1558, 1530, 1482, 1463, 1307, 1248, 806 | *)1.64-1.97(m, 2H), 1.97-3.07(m, 9H), 2.14(s, 3H), 2.31 (s, 3H), 3.24 (dd, 1H), 7.32 (d, 1H), 7.33 (d, 1H), 7.97 (br.s, 1H) | +)23.80(q), 25.74 (t), 30.48(t), 31.89(d), 37.47 (d), 45.61(t), 46.21(q), 53.49 (t), 60.46(t), 110.04(d), 112.42 (d), 119.67(d), 123.18(s), 126.41 (s), 131.82(s), 133.36(s), 133.63 (s), 167.74(s), 192.94(s) |
| SI-WG 600 | H, CN, H, H, H, CH₃ | C₁₈H₁₉N₃O 293.371 | 245 | 1-D | 293(M⁺, 68) 265(7), 248(5), 224(12), 192(10), 155(11), 110(70), 96(100) | 3293, 2938, 2844, 2768, 2220, 1639, 1573, 1537, 1463, 1338, 1262, 1143, 1063, 904, 812 | 1.63-1.98(m, 2H), 1.98-3.43(m, 9H), 2.32(s, 3H), 3.64 (dd, 1H), 7.47 (dd, 1H), 7.54 (dd, 1H), 8.09 (br.s, 1H), 9.41 (br.s, 1H) | 26.27(t), 30.93 (t), 32.33(d), 38.05(d), 46.13 (q), 46.63(t), 54.14(t), 61.10 (t), 103.71(s), 113.20(d), 120.01 (s), 125.36(s), 127.11(d), 127.31 (s), 128.40(d), 134.67(s), 137.59 (s), 193.61(s) |
| SI-WG 591 | H, H, H, H, CH₃, CH₃ | C₁₈H₂₂N₂O 282.388 | amorph | 1-D | 282(M⁺, 60) 254(7), 224(5), 211(8), 182(6), 167(7), 144(53), 110(50), 96(100) | 3400, 3048, 2925, 2788, 1648, 1514, 1466, 1413, 1368, 1255, 1233, 1050, 743 | 1.58-1.93(m, 2H), 1.93-3.06(m, 9H), 2.30(s, 3H), 3.22 (dd, 1H), 3.99 (s, 3H), 7.06-7.31 (m, 2H), 7.31-7.49 (m, 1H), 7.70 (d, 1H) | 26.63(t), 30.96 (t), 31.64(q), 31.82(d), 38.54(d) 46.81(q), 47.96(t), 54.38(t), 61.27(t), 110.19(d), 117.09 (s), 120.01(d), 120.68(d), 125.93 (d), 126.47(s), 133.72(s), 138.81 (s), 195.18(s) |
| SI-WG 422 | H, H, H, | C₁₆H₁₈N₂O | 185 | 1-D | 254(M⁺, 70) | 3328, 3054, | 1.54-1.89(m, 4H), | 26.00(t), 32.07(t) |

TABLE 4-continued

| | | | | | | | | |
|---|---|---|---|---|---|---|---|---|
| | H, H, H | | 254.333 | | | 223(12), 210(22), 196(33), 180(17), 168(40), 155(24), 143(20), 130(74), 115(23), 96(100) | 3020, 2977, 2925, 2905, 2822, 27321 1663, 1572, 1533, 1467, 1327, 740 | 1.98–2.44(m, 2H), 2.54–3.09(m, 6H), 3.26(dd, 1H), 7.06–7.26(m, 1H), 7.26–7.48(m, 2H), 7.70(d, 1H), 9.05 (br.s, 1H) | 33.50(d), 37.80(d) 44.74(t), 46.18(t) 51.69(t), 112. (d), 120.22(d), 120.90(d), 124.62 (s), 126.41(d), 127.48(s), 133.09 (s), 136.46(s), 193.75(s) |
| SI-WG 533 | H, H, H, H, H, n-Pr | $C_{19}H_{24}N_2O$ 296.415 | | 134 | 1-D | 296(M$^+$, 40) 267(41), 172(21), 138(28), 124(50), 86(15), 58(100) | 3315, 2956, 2928, 2896, 2878, 2803, 2776, 2740, 1628, 1530, 1461, 1334, 1227, 738 | 0.93(t, 3H), 1.56 (m, 2H), 1.65–1.91 (m, 2H), 2.00–3.03 (m, 11H), 3.25 (dd, 1H), 7.04–7.29 (m, 1H), 7.29–7.47 (m, 2H), 7.70 (d, 1H), 9.05 (br.s, 1H) | 12.04(q), 20.19(t) 26.46(t), 31.39(t) 33.03(d), 37.64(d) 45.78(t), 52.02(t) 58.85(t), 61.04(t) 112.12(d), 120.19 (d), 120.95(d), 124.92(s), 126.38 (d), 127.47(s), 133.03(s), 136. (s), 193.96(s) |

| Tablet | |
|---|---|
| 1) SI-WG 350.HCl | 10.00 kg |
| 2) Avicel PH 102 | 40.00 kg |
| 3) lactose. 1H$_2$O | 12.85 kg |
| 4) corn starch | 16.00 kg |
| 5) corn starch | 0.50 kg |
| 6) magnesium stearate | 0.25 kg |
| | 80.00 kg |

Working up takes place by mixing 1), 2), 3) and 4) in a kneader granulation mixing apparatus for 20 minutes. Subsequently, 10 l. of a 5% aqueous solution of 5) is added to the mixture and mixed for a further 30 minutes. The mixture is sieved, dried and again sieved. Thereafter, the granulate obtained is mixed with 6) in the above apparatus for 30 minutes and the mass subsequently pressed into tablets with, for example, a diameter of 6 mm. and a weight of 80 mg.

| Ampules | |
|---|---|
| 1) SI-WG 350.HCl | 0.100 kg |
| 2) citric acid monohydrate | 0.470 kg |
| 3) trisodium citrate dihydrate | 0.530 kg |
| 4) sodium chloride | 0.625 kg |
| 5) water for injection purposes | ad 100 l. |

The components 1), 2), 3) and 4) are dissolved in 5) in an appropriate container. The solution is sterile filtered and filled in 1 ml. portions into ampoules; the are steam-sterilized.

Not only for tablets but also for ampules, instead of 1) there can also be used a compound of general formula I, as well as of general formula V.

Pharmacological investigations:

It was found that the said substances change the measured values of circulation function to different extents. The biological test process hereby used is described, inter alia, in: Staff of the Department of Pharmacology, University of Edinburgh, and L. J. McLeod (1970): Pharmacological Experiments in Intact Preparations, Churchill Livingstone, Edinburgh, London and New York, page 62.

10 mg kg$^{-1}$ doses of the compounds according to the invention, in the form of the hemi-tartrate were administered intravenously to rats in groups of 6 to 8 animals. 0.9% sodium chloride solution served as solvent for the compounds. 0.9% sodium chloride solution was injected as control substances. Before commencement of the experiment and at the end of the experiment, blood samples were taken and the blood gas concentrations determined.

After administration of the compounds to narcotized rats, the changes of blood pressure and of heart rate were monitored over a period of 2 hours and the maximum effect determined in each case. The results are summarized in Table 5.

It can be seen that the compounds according to the invention bring about a dosage-dependent heart rate and blood pressure reduction in rats.

Furthermore, this action could be found for the compounds according to the invention, in particular for SI-WG 350, where alternative methods of administration were employed and, on other species of experimental animals. In the case of intraduodenal administration to the rat and to the cat the lower active does is 1 mg. kg$^{-1}$.

The claimed compounds in the cardivascular-effective dosage range influence neither spontaneous behavior nor spontaneous mobility, nor are they analgesically active, as could be demonstrated by appropriate investigations by usual techniques in mice.

Even after despinalization in rats, both blood pressure reduction and also heart rate decrease was initiated by SI-WG 350, as well as by other compounds according to the invention.

These results, as well as investigations on isolated, spontaneously beating guinea pig right auricles and left auricles stimulated with 1 Hz confirmed that the claimed compounds possess a direct working mechanism on the heart. The test process employed is described, inter alia, in: Staff of the Department of Pharmacology, University of Edinburgh (1970): Pharmacological Experiments on Isolated Preparation, Churchill Livingston, Edinburgh, London and New York, page 112.

Animals having a body weight of about 500 g, were used and were divided into groups of 4 animals each. The compounds to be tested were dissolved in tyrode solution/sodium chloride solution 50:50 v/v and the desired concentration adjusted in the bath liquid. The experiment was carried out in the known manner. The results are summarized in Table 6.

In usual investigation methods on anesthetized rats, it could be demonstrated that the claimed substances possess no interaction with histaminergic or cholesteric mechanisms. In the same way, they did not cause any beta-adrenoreceptor-blocking effect so that investigations with regard to a possible influencing of α-antagonistic effectiveness was determined on female beagles with a body weight of about 15 kg. The compounds to be tested (in the form of the hemi-tartrates) were taken up in the tyrode solution, phentolamine serving as a reference substance (reference antagonist). As control, tyrode solution was used alone. The reference antagonist was DL-noradrenaline hydrochloride.

The preparation of blood vessel sections and further experimentation took place in a known manner. The quantitative evaluation and calculation took place according to the method of J. M. Van Rossum (Arch. int. Pharmacodyn., 143 (3–4), 299–300/1963) and H. O. Schild (pharmacol. Rev., 9 242/1957 . the results are, for example, summarized in the following Table:

| Compound | $PA_2 \pm s$ |
| --- | --- |
| SI-WG 350 | 6.88 ± 0.73 |
| SI-WG 357 | 6.88 ± 0.27 |
| phentolamine | 7.19 ± 0.68 |

The α-adrenoreceptor-specific point of attach of the compounds was reinforced by receptor binding/displacement studies in which, for the compound SI-WG 350, a 50% displacement ($IC_{50}$ value) of the labelled ligand $^3$H-prozoin at a concentration of $3.3 \cdot 10^{-8}$ M was ascertained (phentolamine = $1.8 \times 10^{-8}$ M.). No interference on $\alpha_2$-receptors in competition with $^3$H-prazosine was found. Similar test processes with the corresponding ligands demonstrated an absence of competition for β-receptors and calcium- and sodium-specific binding sites.

TABLE 5

| COMPOUND | DOSAGE | CHANGE OF HEART FREQUENCY (%) | BLOOD PRESSURE CHANGE AVERAGE PRESSURE (%) |
| --- | --- | --- | --- |
| SI-WG 350 | 1 mg/kg i.v. | −14.5 | −15.8 |
| | 2 mg/kg i.v. | −21.9 | −16.5 |
| | 5 mg/kg i.v. | −28.4 | −31.5 |
| | 2 mg/kg i.d. | −7.2 | −19.2 |
| | 5 mg/kg i.d. | −23.0 | −25.7 |
| SI-WG 357 | 5 mg/kg i.v. | −6.1 | −11.6 |
| | 10 mg/kg i.v. | −5.5 | −22.9 |
| SI-WG 334a | 2 mg/kg i.v. | −21.2 | −17.2 |
| | 5 mg/kg i.v. | −19.6 | −25.9 |
| | 10 mg/kg i.v. | −20.8 | −30.1 |
| SI-WG 360 | 2 mg/kg i.v. | −10.7 | −10.3 |
| | 5 mg/kg i.v. | −14.3 | −23.0 |
| | 10 mg/kg i.v. | −22.2 | −34.2 |
| SI-WG 331 | 5 mg/kg i.v. | — | — |
| | 20 mg/kg i.v. | −9.7 | −18.4 |
| | 50 mg/kg i.v. | −19.3 | −29.1 |
| SI-WG 379 | 5 mg/kg i.v. | −17.4 | −19.2 |
| | 10 mg/kg i.v. | −23.9 | −22.0 |
| SI-WG 399 | 2 mg/kg i.v. | — | — |
| | 5 mg/kg i.v. | −6.6 | — |
| | 10 mg/kg i.v. | −12.1 | — |
| SI-WG 419 | 2 mg/kg i.v. | −7.5 | −10.6 |
| | 5 mg/kg i.v. | −12.1 | −21.4 |
| | 10 mg/kg i.v. | −22.8 | −26.7 |
| SI-WG 449 | 2 mg/kg i.v. | — | −16.0 |
| | 5 mg/kg i.v. | −12.0 | −10.0 |
| | 10 mg/kg i.v. | −17.0 | −22.0 |
| SI-WG 454 | 1 mg/kg i.v. | −7.6 | −4.8 |
| | 2 mg/kg i.v. | −9.0 | −6.8 |
| | 5 mg/kg i.v. | −20.3 | −7.4 |
| SI-WG 578 | 1 mg/kg i.v. | — | — |
| | 2 mg/kg i.v. | −6.2 | — |
| | 5 mg/kg i.v. | −10.2 | +2.0 |
| SI-WG 562 | 2 mg/kg i.v. | — | −3.4 |
| | 5 mg/kg i.v. | — | −9.4 |
| | 10 mg/kg i.v. | −6.0 | −12.4 |
| SI-WG 583 | 2 mg/kg i.v. | −3.4 | +2.3 |
| | 5 mg/kg i.v. | −10.0 | −11.7 |
| | 10 mg/kg i.v. | −11.2 | −12.0 |
| SI-WG 587 | 2 mg/kg i.v. | — | — |
| | 5 mg/kg i.v. | — | +12.2 |
| | 10 mg/kg i.v. | −4.8 | +11.6 |
| SI-WG 571 | 2 mg/kg i.v. | −1.4 | — |
| | 5 mg/kg i.v. | — | — |
| | 10 mg/kg i.v. | −11.6 | −14.1 |
| SI-WG 625 | 1 mg/kg i.v. | — | — |
| | 2 mg/kg i.v. | — | — |
| | 5 mg/kg i.v. | −8.4 | −9.4 |
| SI-WG 604 | 5 mg/kg i.v. | — | — |
| | 10 mg/kg i.v. | — | −10.7 |
| | 20 mg/kg i.v. | — | −15.6 |
| SI-WG 600 | 2 mg/kg i.v. | — | +9.5 |
| | 5 mg/kg i.v. | −8.9 | −6.0 |
| | 10 mg/kg i.v. | −9.4 | 04.8 |
| SI-WG 422 | 5 mg/kg i.v. | — | — |
| | 10 mg/kg i.v. | −12.8 | — |
| | 20 mg/kg i.v. | −15.5 | 21.8 |
| SI-WG 533 | 5 mg/kg i.v. | −9.7 | −20.1 |
| | 10 mg/kg i.v. | −17.9 | −22.7 |
| | 20 mg/kg i.v. | −19.8 | −37.4 |

TABLE 6

| | | Maximum effect in % of initial value | |
| --- | --- | --- | --- |
| COMPOUND | DOSAGE | LEFT AURICLE INTROPIC | RIGHT AURICLE CHRONOTROPIC |
| SI-WG 350 | 2.0 μg/ml | +16 | −25 |
| | 10.0 μg/ml | +17 | −31 |
| | 20.0 μg/ml | +23 | −47 |
| SI-WG 331 | 2.0 μg/ml | +8 | −7 |
| | 10.0 μg/ml | +14 | −12 |
| | 20.0 μg/ml | +31 | −23 |
| SI-WG 334a | 2.0 μg/ml | +26 | −14 |
| | 10.0 μg/ml | +25 | −29 |
| | 20.0 μg/ml | +33 | −43 |
| SI-WG 357 | 2.0 μg/ml | +17 | −9 |
| | 10.0 μg/ml | +32 | −19 |
| | 20.0 μg/ml | +24 | −19 |
| SI-WG 360 | 2.0 μg/ml | +17 | −10 |
| | 10.0 μg/ml | +39 | −29 |
| | 20.0 μg/ml | +50 | −41 |
| SI-WG 379 | 0.5 μg/ml | +8 | −14 |
| | 2.0 μg/ml | +24 | −35 |
| | 4.0 μg/ml | +24 | −46 |
| | 10.0 μg/ml | +23 | −81 |
| SI-WG 399 | 0.5 μg/ml | ±5 | −22 |
| | 2.0 μg/ml | +25 | −43 |
| | 4.0 μg/ml | +13 | −66 |
| | 10.0 μg/ml | ±5 | −83 |
| SI-WG 419 | 0.5 μg/ml | +6 | −18 |
| | 2.0 μg/ml | +6 | −30 |
| | 4.0 μg/ml | −7 | −42 |
| | 10.0 μg/ml | −27 | −80 |
| SI-WG 449 | 2.0 μg/ml | +16 | −19 |
| | 10.0 μg/ml | +23 | −40 |
| | 20.0 μg/ml | +20 | −57 |
| SI-WG 454 | 2.0 | −7.9 | −26.4 |
| | 10.0 | −11.4 | −65.1* |
| | 20.0 | −33.3 | −72.7* |
| SI-WG 578 | 2.0 | −3.6 | −19.4 |
| | 4.0 | −12.1 | −28.1 |
| | 10.0 | −10.9 | −52.9* |
| SI-WG 562 | 2.0 | −4.1 | −11.3 |
| | 4.0 | −6.0 | −15.7 |

TABLE 6-continued

| COM-POUND | DOSAGE | LEFT AURICLE INTROPIC | RIGHT AURICLE CHRONOTROPIC |
|---|---|---|---|
| | 10.0 | −7.4 | −31.8 |
| SI-WG 583 | 2.0 | — | −16.1 |
| | 4.0 | −5.1 | −23.7 |
| | 10.0 | −14.9 | −30.3 |
| SI-WG 587 | 4.0 | +14.9 | −10.4 |
| | 10.0 | +29.4 | −13.9 |
| | 20.0 | +31.8 | −19.8 |
| SI-WG 571 | 2.0 | — | −3.1 |
| | 4.0 | −3.9 | −8.4 |
| | 10.0 | −11.4 | −9.1 |
| SI-WG 625 | 2.0 | — | −13.8 |
| | 4.0 | −4.7 | −17.4 |
| | 10.0 | −8.9 | −26.3 |
| SI-WG 600 | 2.0 | 12.4 | −25.2 |
| | 4.0 | 23.0 | −32.7 |
| | 10.0 | 30.0 | −49.1 |
| SI-WG 604 | 10.0 | 9.8 | −10.2 |
| | 20.0 | 8.2 | −15.6 |
| | 60.0 | 13.8 | −24.7 |
| SI-WG 422 | 0.5 | −4.2 | −6.7 |
| | 2.0 | −12.2 | −19.3 |
| | 4.0 | −14.9 | −36.1 |
| SI-WG 591 | 2.0 | 11.8 | −20.0 |
| | 4.0 | 12.0 | −31.9 |

TABLE 6-continued

| COM-POUND | DOSAGE | LEFT AURICLE INTROPIC | RIGHT AURICLE CHRONOTROPIC |
|---|---|---|---|
| | 10.0 | 27.4 | −43.9 |
| SI-WG 533 | 2.0 | 11.1 | −15.9 |
| | 4.0 | 18.1 | −26.0 |
| | 10.0 | 17.0 | −34.1 |

Compatibility

The compatibility of the compounds according to the invention is very good. The measured acute toxicity in the case of peroral administration to mice is from 150 to 225 mg/kg. In the case of intravenous administration, the $LD_{50}$ in mice is from 24.0 to 34.0 mg./kg.

Taking into account the determined $LD_{50}$ values and the therapeutic human dosage, then there is a very good therapeutic breadth.

We claim:

1. The compound of the formula:

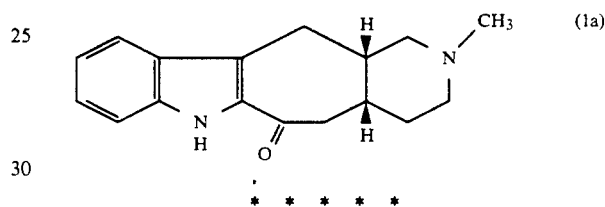

(1a)

* * * * *

UNITED STATES PATENT AND TRADEMARK OFFICE
CERTIFICATE OF CORRECTION

PATENT NO. : 5,159,080
DATED : October 27, 1992
INVENTOR(S) : Klaus Görler et al It is certified that error appears in the above-identified patent and that said Letters Patent is hereby corrected as shown below:

On the title page, item [75] inventors, change "Goler" to --Gorler--.

Col. 11, line 23, for: SI-WG, the mgp °C should be --0-- not "1".

Col. 12, line 47, Table 2, under "SI-WG 420" right column is missing --(m,8H), 7.68 (d,1H)-- not "(m,8H), 3H), 1H)".

Col. 12, line 57, Table 2, Under "SI-WG 452" after "3.60 (dd" insert --1H)--.

Col. 14, line 2, Table 2, under SI-WG 560, after "(s,3", insert --1H)--.

Col. 14, line 20, Table 2, Under "SI-WG 581" column "IR KBr (cm$^{-1}$", after "1574, 1536" insert --1255, 1129 1065, 729--.

Col. 13, line 32, Table 2, Under "SI-WG 598" column "MS...%)" "309 ($^+$.1)" should read --309 (M$^+$.1)--.

Col. 13, line 52, Table 3, Under "SI-WG 359" of double bond", "4a-4" should read --4a-5--.

Col. 13, line 52, Table 3, Under "SI-WG 359", column "prepa. acc example", all the data on that line, beginning with "266 (m$^+$,100)" should be moved over one column, and --4-- should be inserted under the "prepa. acc Example column.

UNITED STATES PATENT AND TRADEMARK OFFICE
CERTIFICATE OF CORRECTION

PATENT NO. : 5,159,080
DATED : October 27, 1992
INVENTOR(S) : Klaus Görler

It is certified that error appears in the above-identified patent and that said Letters Patent is hereby corrected as shown below:

Col. 13, line 52, Table 3, move entire line over one column per previous correction.

Col. 16, line 32, table 3, Under "SI-WG 421" column "$^1$H-NMR (CDCl$_3$)", delete one line "3.54 (s, 2H)", it is repeated twice on patent copy.

Col. 16, line 59, Table 3, Under "SI-WG 461" right column, "48.84 (t)" should read --48.85 (t)--.

Col. 18, line 14 last 3 columns on the right, Under "SI-WG 582" move 3rd line over to the left - "(10 258 (38)" "2782, 1649" "3.04 (s, 2H)".

Col. 20, line 58, Table 4, Under "SI-WG 462", "133.29(d)" should read --113.29(d)--.

Col. 24, line 2, Table 4, Under "SI-WG 422", "112." should read --112.10--.

Col. 24, line 18, Table 4, Under "SI-WG 533", "136." should read --136.47--.

Col. 23, line 64, "10 mg kg$^{31}$ $^1$" should read --10 mg. kg$^{-1}$--.

Col. 24, line 41, "10 mg kg$^{31}$ $^1$" should read --10 mg. kg$^{-1}$--.

UNITED STATES PATENT AND TRADEMARK OFFICE
CERTIFICATE OF CORRECTION

PATENT NO. : 5,159,080

DATED : October 27, 1992

INVENTOR(S) : Klaus Görler et al

It is certified that error appears in the above-identified patent and that said Letters Patent is hereby corrected as shown below:

Col. 26, line 26, Table 5, Under "SI-WG 600" "04.8"
                          should read -- -4.8--.

Signed and Sealed this

Twenty-second Day of November, 1994

*Attest:*

BRUCE LEHMAN

*Attesting Officer*   *Commissioner of Patents and Trademarks*